(12) United States Patent
Dahners

(10) Patent No.: US 6,379,359 B1
(45) Date of Patent: Apr. 30, 2002

(54) PERCUTANEOUS INTRAFOCAL PLATE SYSTEM

(75) Inventor: Laurence E. Dahners, Chapel Hill, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/566,187

(22) Filed: May 5, 2000

(51) Int. Cl.$^7$ ................................................ A61B 17/72
(52) U.S. Cl. ........................................... 606/62; 606/69
(58) Field of Search ............................ 606/60, 62, 69, 606/72, 74

(56) References Cited

U.S. PATENT DOCUMENTS

| | | | | |
|---|---|---|---|---|
| 4,535,764 A | * | 8/1985 | Ebert | |
| 5,709,682 A | * | 1/1998 | Medoff | 606/60 |
| 6,248,109 B1 | * | 6/2001 | Stoffella | 606/75 |

FOREIGN PATENT DOCUMENTS

SU          1057026 A   * 11/1983   ................. 606/72

* cited by examiner

Primary Examiner—Jeffrey A. Smith
(74) Attorney, Agent, or Firm—Jenkins & Wilson, P.A.

(57) ABSTRACT

An intrafocal plate and method of use for securing bone fractures comprising an elongated plate element having a flat plate surface at one end thereof defining a top surface and a bottom surface and a leading end and a trailing end. A longitudinally extending resilient body element depends from the trailing end of the flat plate surface so as to define a shoulder at the juncture of the body element and the flat plate surface and a pin at the other end of the body element. The intrafocal plate is formed so that a force applied at the pin end causes a force to be applied in the opposite direction at the flat plate surface. The intrafocal plate is particularly intended for use to secure metaphyseal bone fractures by having the body element of the intrafocal plate inserted into the tubular hollow of the bone through the fracture site so as to cause the shoulder of the intrafocal plate to seat in the fracture site and urge the flat plate surface of the plate element against the outside surface of the bone.

15 Claims, 5 Drawing Sheets

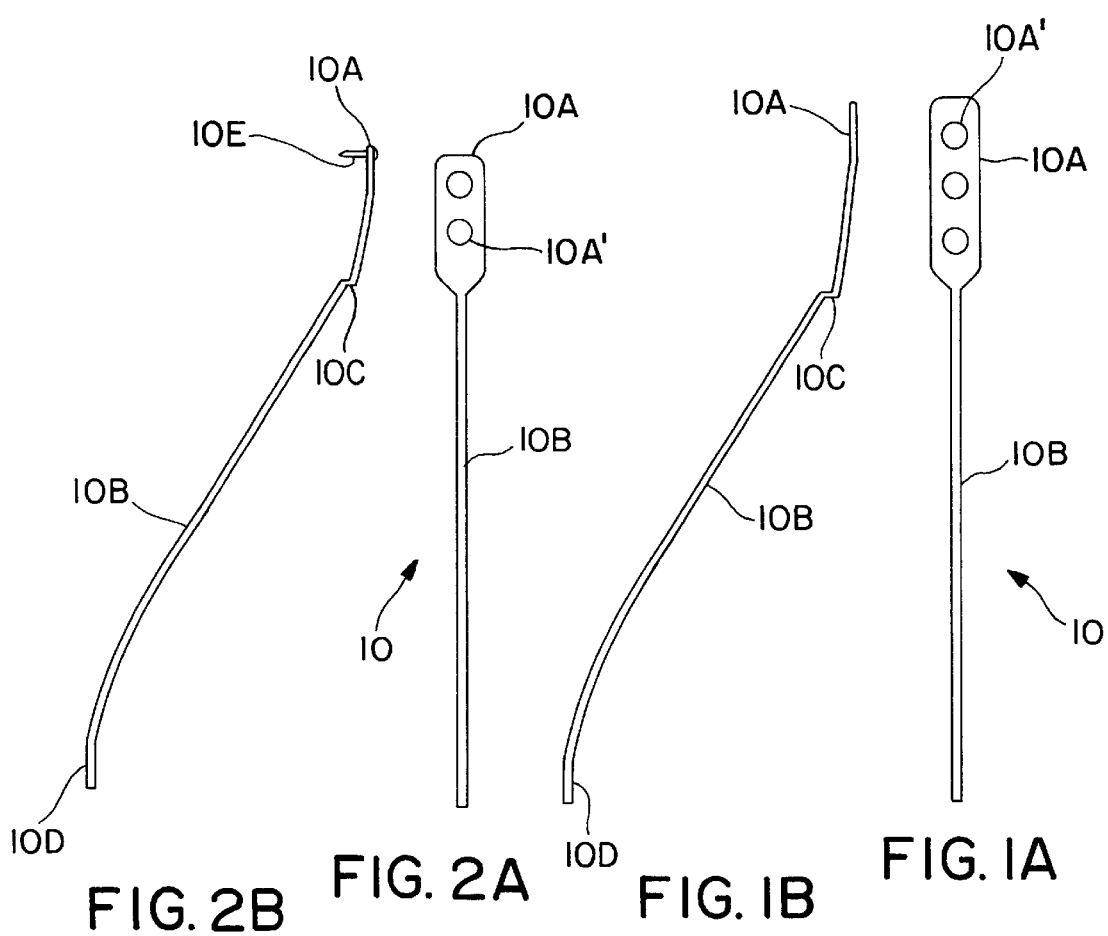

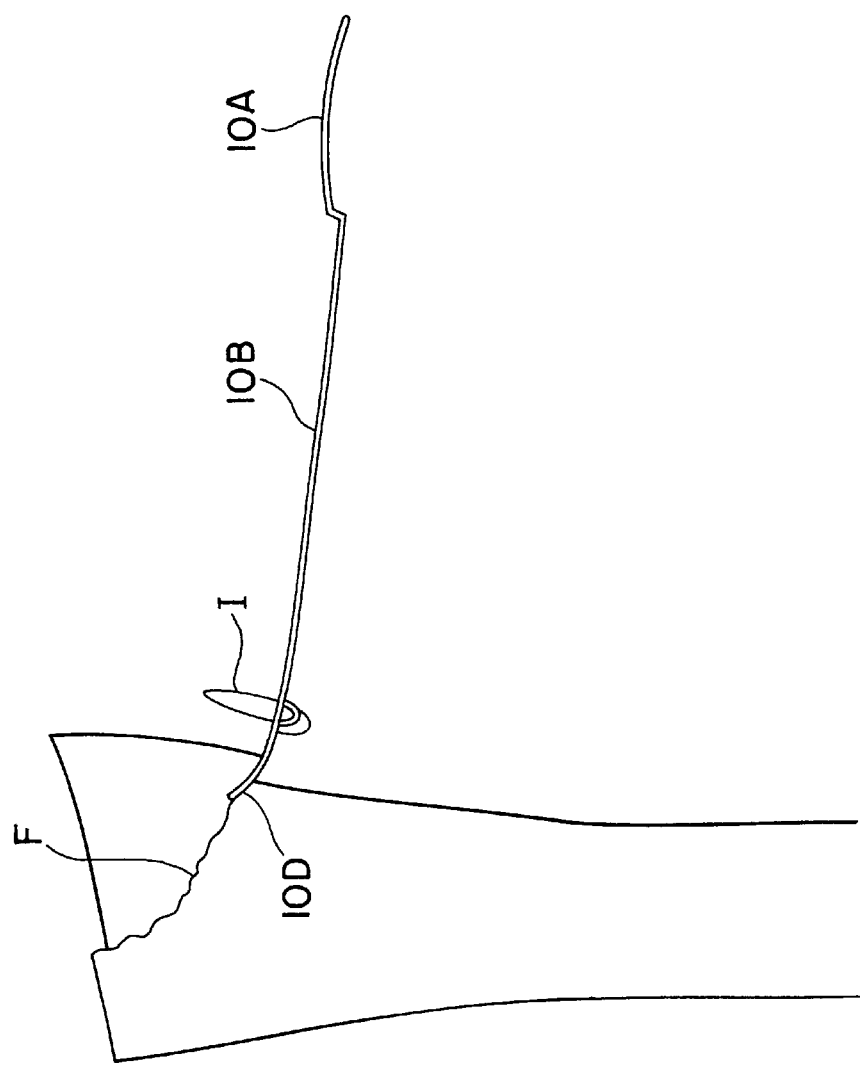
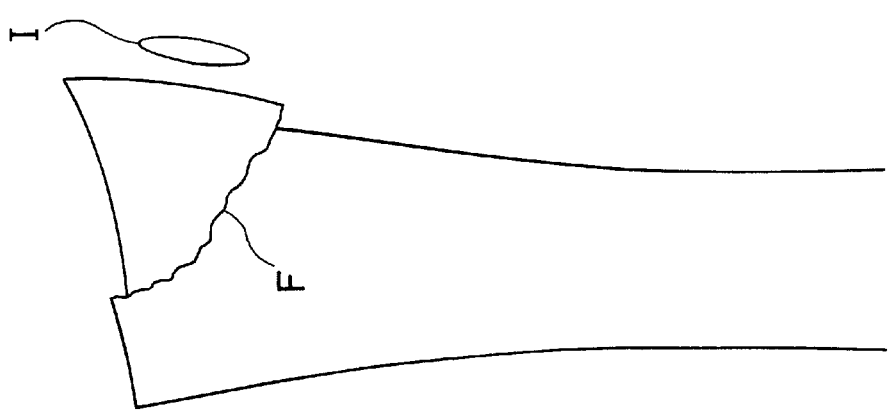
FIG. 5A
FIG. 5B

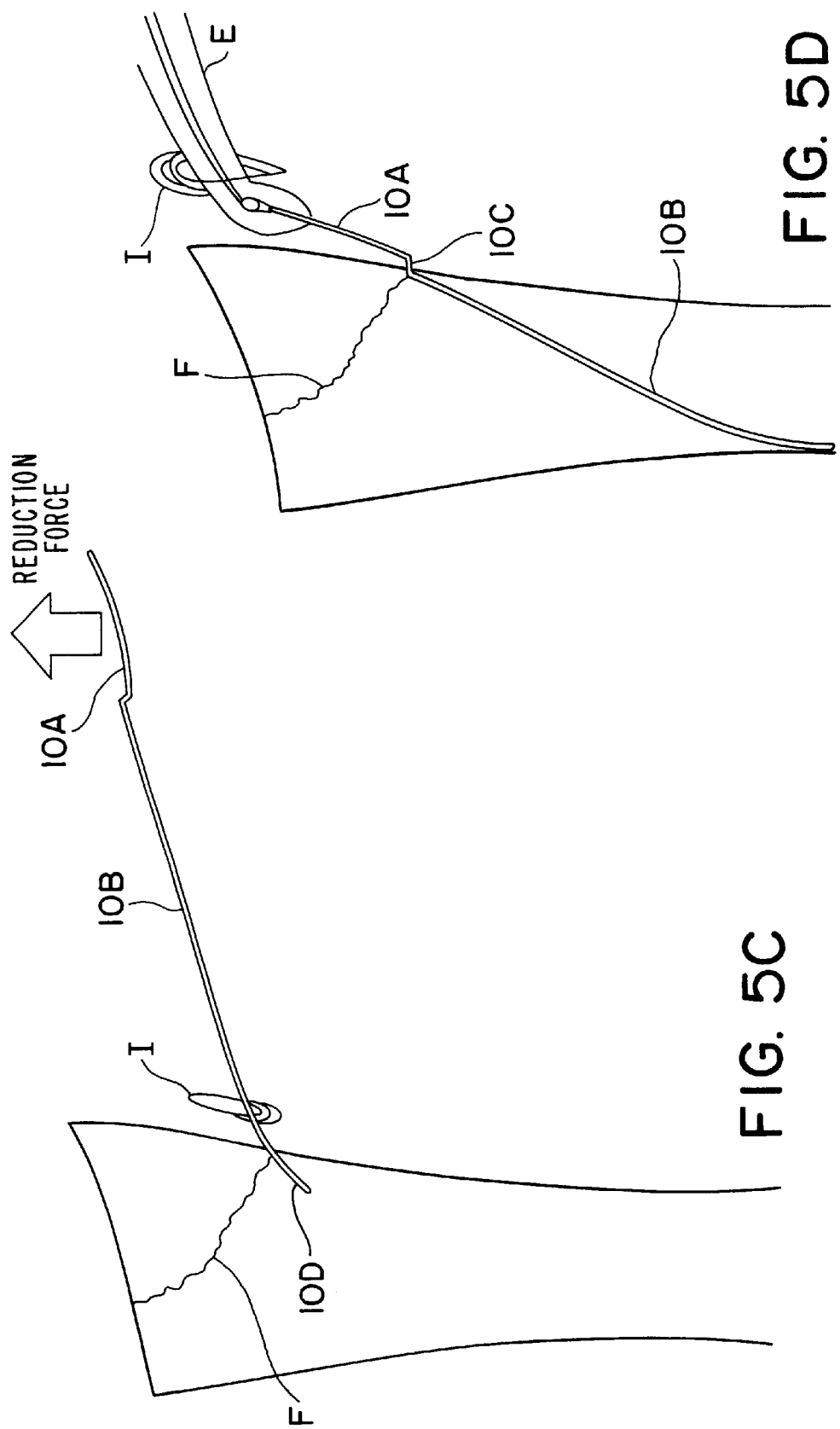

PERCUTANEOUS INTRAFOCAL PLATE SYSTEM

TECHNICAL FIELD

The present invention relates generally to surgical apparatuses and methods, and more particularly, to a percutaneous intrafocal plate surgical apparatus and method.

RELATED ART

There are a variety of apparatuses and methods presently being used to address metaphyseal fractures. As is well known to those skilled in the art, metaphyseal fractures consist of fractures near the end of a bone in the area of the junction between the tubular shaft of the bone and the spongy, blocky, end portions of the bone known as the metaphysis and epiphysis. Bone fractures in this metaphyseal area, especially fractures that are oblique, tend to cause the fragment to be pulled off to one side of the shaft by the forces applied by the muscles which are, in effect, continually attempting to shorten the bone. A variety of apparatuses and methods for surgically addressing metaphyseal fractures have been developed and are well known in the medical arts. Examples of such apparatuses and methods include, for example, casts, external fixators, pins and plates. Each of these will be discussed hereinafter for a better understanding of the state of the art in apparatuses and methods for addressing metaphyseal bone fractures.

Casts

Casts are used to align metaphyseal fractures that are transverse and to prevent the bone sections from falling off to the side. However, when a fracture is not transverse but oblique, the fracture tends to shorten within the cast and thereby allow displacement and an unsatisfactory outcome. Although casts are often attempted with fractures which might otherwise be treated with the apparatus and method of the invention described and claimed hereinafter, they are frequently unsuccessful and subsequently require that the patient be treated surgically to effect a satisfactory outcome.

External Fixators

External fixators are devices which consist of pins implanted in the bone on opposing sides of the fracture and connected with a metal frame which is external to the patient's limb. The pin insertion site where the pin penetrates the skin and underlying fat, muscle and the like on its way to insertion into the bone becomes a source of pain for a patient as well as a site of infection due to the chronically open wound about the pin during the time that the fracture is healing. Furthermore, in one of the most common locations for this kind of fracture, the distal radius, the pins often irritate the tendons which pass over and about the bone and thus induce stiffness of the fingers because of the patient's reluctance to move his fingers and thereby induce pain from the tendons.

Pins

Percutaneous pins are often used to treat metaphyseal fractures and, in fact, some of the percutaneous pins are inserted intrafocally. These are called "Kapandji" pins. These pins are usually left sticking out through the skin and thus, similarly to the external fixators discussed above, serve as a source of infection and as a source of pain and irritation to neighboring tendons. Pins can, however, be inserted through a small incision and provide an excellent reduction for some metaphyseal fractures.

Plates

Metaphyseal fractures can be addressed quite well with conventional plates. However, a large incision is required to implant a plate and this is known to result in a large scar. Moreover, the plate is known to be a large, broad and lumpy device which can be prominent underneath the underlying tendons and skin and soft tissue, and thus it can many times be painful. In addition, tendons which traverse over plates are often irritated by the plates and this can lead to stiffness.

Thus, despite the existence of a wide variety of conventional apparatuses and methods for surgically addressing a metaphyseal fracture, there remains much room for improvement in the art, particularly for a percutaneous intrafocal plate apparatus and method which is simple, safe and effective for addressing a metaphyseal fracture and which is inserted percutaneously or through a very small incision, that does not protrude through the skin, and which presents a low profile so as not to irritate overlying tissue.

DISCLOSURE OF THE INVENTION

In accordance with the present invention, an intrafocal plate apparatus and method are provided for addressing metaphyseal and similar bone fractures. The apparatus comprises an elongated plate element having a flat plate surface at one end thereof defining a top surface and a bottom surface and a leading end and a trailing end. A longitudinally extending resilient body element depends from the trailing end of the flat surface and defines a shoulder at one end which joins the flat plate surface and an arcuate pin at the other end. The intrafocal plate is formed so that a force applied at the arcuate pin end causes a force to be applied in the opposite direction at the flat plate surface.

Also, in accordance with the present invention, a method for addressing a metaphyseal or similar type of bone fracture is provided utilizing the intrafocal plate described herein above. In a preferred embodiment, the method according to this invention comprises the initial step of providing an intrafocal plate as described herein before. The pin end of the elongated plate element is inserted through a skin incision formed proximate to the metaphyseal bone fracture site and the pin end is intrafocally inserted into the fracture site. Next, the elongated plate element is manipulated as necessary in order to lever the metaphyseal fracture into a reduced position. Finally, the body element of the elongated plate element is pushed into the tubular hollow of the fractured bone such that the pin will resiliently contact the inside wall surface of the tubular hollow at a site opposing the fracture site and thereby cause the shoulder of the elongated plate element to seat in the fracture site and urge the flat plate surface of the elongated plate element against the outside surface of the bone.

It is therefore an object of the present invention to provide a novel intrafocal plate for addressing metaphyseal and similar type fractures and a method for using the same.

It is another object of the present invention to provide an intrafocal plate apparatus and method for using same which can safely and effectively be utilized to address metaphyseal and similar type fractures.

It is another object of the present invention to provide an intrafocal plate apparatus and method for using same which is inserted percutaneously or through a small incision so as not to protrude through the skin and which is stable in use and low profile in construction so as not to irritate overlying tissue.

Some of the objects of the invention having been stated herein above, other objects will become evident as the description proceeds, when taken in connection with the accompanying drawings as best described herein below.

BRIEF DESCRIPTION OF THE DRAWINGS

FIGS. 1A, 1B of the drawings are a front elevation view and side elevation view, respectively, of the intrafocal plate according to the present invention;

FIGS. 2A, 2B of the drawings are a front elevation view and a side elevation view, respectively, of a second embodiment of the intrafocal plate according to the present invention;

FIGS. 5A–5D of the drawings are schematic views of the method of the present invention utilizing the intrafocal plate of FIGS. 1A, 1B to secure a radial styloid fracture;

DETAILED DESCRIPTION OF THE INVENTION

Figures 3, 4A, 4B:
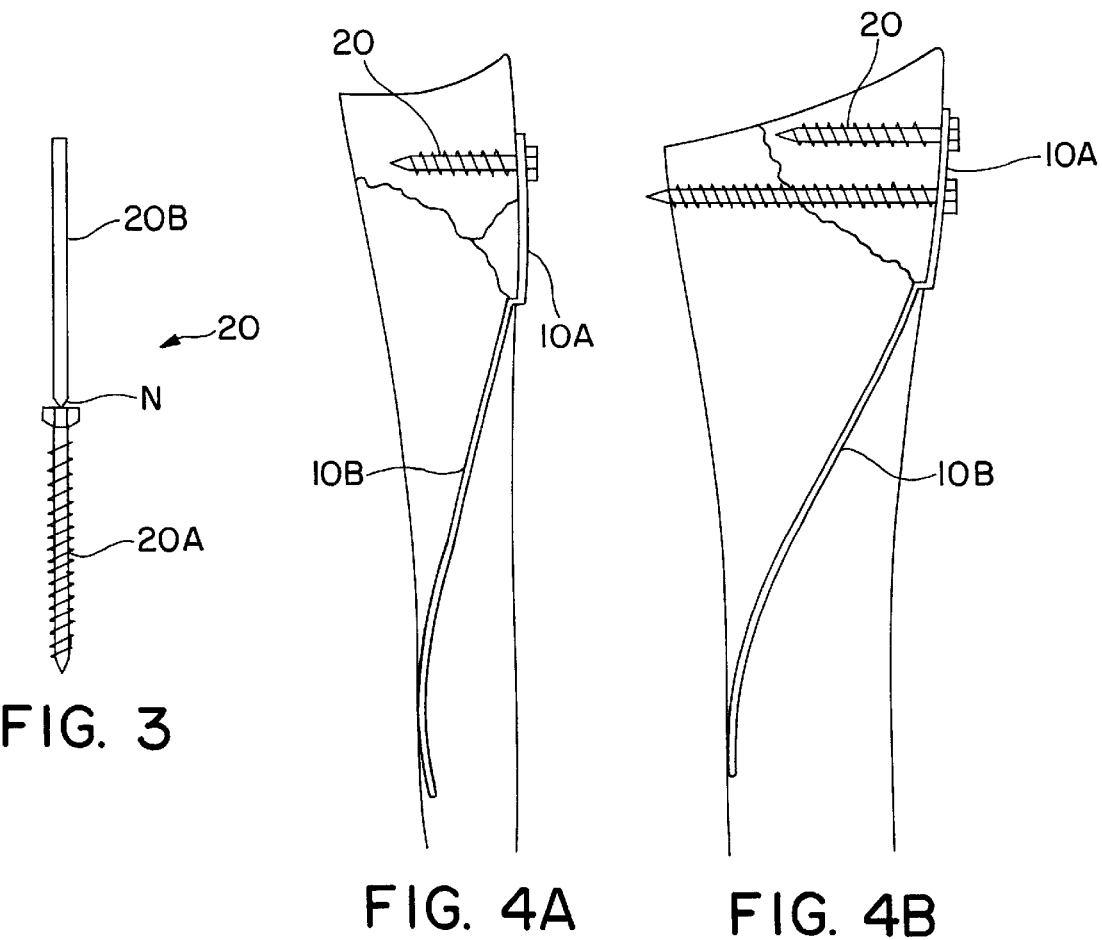
FIG. 3 of the drawings is a side elevation view of a break-away screw which can optionally be used with the intrafocal plates shown in FIGS. 1A, 1B and FIGS. 2A, 2B.
FIGS. 4A, 4B of the drawings show the intrafocal plate of FIG. 1A, 1B used with screw(s) to secure a Colles fracture and a radial styloid fracture, respectively.

A novel intrafocal plate apparatus and method for using the same to address a metaphyseal bone fracture or the like are provided in accordance with the present invention. Referring now to FIGS. 1A, 1B through FIGS. 6A, 6B of the drawings, the percutaneous intrafocal plate apparatus 10 and the method of use of apparatus 10 will now be described in detail.

Intrafocal plate 10 is intended to solve many of the problems of prior art devices for addressing metaphyseal bone fractures (and other similar fractures) by being inserted percutaneously, or through a very small incision, so as not to be left protruding through the skin. Apparatus 10 is particularly advantageous since it is a low profile device that will not tend to irritate overlying tissue.

Apparatus 10 comprises a plate element 10A top portion, a downwardly and inwardly extending body element 10B. Body element 10B of apparatus 10 forms a shoulder 10C at one end at its juncture with plate element 10A and an arcuate pin 10D at the other end thereof. Referring particularly to FIGS. 1A, 1B, it will be appreciated that plate element 10A defines one or more apertures 10A' therein (applicant contemplates from 1 to 4 apertures) to facilitate affixation of intrafocal plate 10 to a bone in a manner to be described hereinafter. Although one or more apertures 10A' may be provided in plate element 10A of intrafocal plate 10, applicant contemplates that the intrafocal plate could be affixed to a metaphyseal fracture using the methodology described hereinafter without the necessity for one or more screws, or in other words that the use of screws in combination with intrafocal plate 10 is optional. Further, applicant contemplates that apparatus 10 can be formed without shoulder 10C at the juncture of body element 10B and plate element 10A as a matter of design choice; however, applicant believes it preferable to incorporate shoulder 10C into apparatus 10.

Referring now to FIGS. 2A, 2B, wherein like numbers represent like parts, intrafocal plate 10 will be understood to be formed from plate element 10A and body element 10B wherein the top portion of body element 10B forms shoulder 10C at its juncture with plate element 10A and an arcuate pin 10D at its other end. Additionally, in this alternative embodiment of the invention, applicant contemplates that plate element 10A may be provided with one or more spikes 10E depending outwardly from the bottom surface of plate element 10A to facilitate affixation of intrafocal plate 10 to a metaphyseal fracture. Although applicant does not believe the invention requires providing one or more apertures in plate element 10A, it is preferable that this embodiment of the invention incorporate both one or more apertures 10A' in plate element 10A in addition to one or more spikes 10E. Shoulder 10C is also optional in this embodiment of apparatus 10, but applicant believes it preferable to incorporate shoulder 10C into the apparatus to enhance seating of apparatus 10 in the fracture site as described hereinafter.

FIG. 3 depicts a screw, generally designated 20, which can be used in combination with intrafocal plate 10 if so desired by a surgeon. As noted herein before, the insertion of one or more screws 20 through apertures 10A' of intrafocal plate 10 is optional and is not required by the apparatus of the invention. Referring again to FIG. 3, it will be appreciated that screws 20 are provided with a threaded portion 20A and a stem portion 20B which define a neck N at the juncture thereof. Thus, the neck at the juncture of the threaded portion 20A and the stem portion 20B will allow the stem or pin to be broken off the screw after insertion by the physician. This facilitates easy insertion of screw 20 through intrafocal plate 10 and the bone thereunder, and then removal of the stem or pin 20B so that no portion of screw 20 will be left protruding through the skin.

Referring now to FIG. 4A, intrafocal plate 10 can be seen implanted in a typical Colles fracture of the distal radius, and FIG. 4B shows intrafocal plate 10 planted in a radial styloid fracture. In both FIGS. 4A and 4B, it can be seen that the fracture is somewhat oblique and thus, muscle will attempt to shorten the bone and tend to force the bone fragments to slide laterally to the right. Intrafocal plate 10 when affixed to the fracture site will prevent this sliding from taking place. Screws 20 may optionally be used with intrafocal plate 10 as necessary, and their use may keep intrafocal plate 10 from sliding in or out of the bone and may hold the bone fragment in a more secure position in certain situations. It will be appreciated that in the second embodiment of the invention, intrafocal plate 10 shown in FIGS. 2A, 2B may be used to address the fracture shown in FIGS. 4A, 4B and the spikes 10E thereof would also serve to keep the plate in a secure position affixed to the bone of the fracture site.

Also in accordance with present invention, the method for securing a metaphyseal bone fracture or the like is provided utilizing intrafocal plate 10 as described herein above. In a preferred embodiment, the method according to this invention can be appreciated with reference to FIGS. 5A–5D which demonstrate the insertion of pin end 10D into a radial styloid fracture similar to that shown in FIG. 4B. The method of insertion of intrafocal plate 10 is similar regardless of the type of fracture that is being addressed, although applicant contemplates that intrafocal plate 10 will normally be used to address metaphyseal bone fractures.

Referring to FIG. 5A, a skin incision I is made more proximate to the end of the bone than the actual fracture site F. In FIG. 5B, pin end 10D of intrafocal plate 10 is inserted through incision I, tugging the incision somewhat proximal on the radius so that pin end 10D can be inserted into the fracture site F. This can be done by palpation and with fluoroscopic guidance without actually seeing fracture site F and therefore using a very small incision. As shown in FIG. 5B, arcuate pin end 10D is inserted 180 degrees rotated relative to the position in which it will eventually lie so that it is easier to slip into fracture site F. In FIG. 5C, once pin 10D is inserted into fracture site F, intrafocal plate 10 is rotated 180 degrees to put the curve of pin end 10D back proximally along the shaft of the radius. As plate element 10A of intrafocal plate 10 is pushed distally, fracture site F is itself reduced by the leverage force applied by pin end 10D. This also takes tension off of skin incision I so that it is not pulled as far proximately as was done initially. Pin end 10D is then pushed down into the tubular hollow of the more proximal portion of the bone as shown in FIG. 5D.

FIG. 5D shows pin end 10D of intrafocal plate 10 completely inserted and held with an insertion tool (similar to a small angled pliers). Pin end 10D of intrafocal plate 10 is resiliently urged against the remote back wall of the tubular hollow from the fracture site as also shown in FIG. 5D. Shoulder 10C of intrafocal plate 10 between plate element 10A and pin end 10D is now seated in fracture site F so as to keep intrafocal plate 10 from sliding further into the bone or from sliding out of the bone, and also the shoulder helps to avoid a tendency to over-reduce the fracture site. Once intrafocal plate 10 is fully inserted into the fracture site and bone, the insertion tool can be removed so as to allow plate element 10A of intrafocal plate 10 to snap back against the bone and skin incision I to fall back into place. At this point, intrafocal plate 10 may be stable without a screw 20 being used to affix intrafocal plate 10 to the bone. However, one or more screws 20 may be inserted to ensure that intrafocal plate 10 does not slide in or out of the fracture site and to further stabilize the fracture fragment against shortening or lateral displacement. The alternative embodiment of intrafocal plate 10 shown in FIGS. 2A, 2B is used in the same manner as the first embodiment of the invention, but one or more spikes 10E depending from the bottom surface of plate element 10A will serve to secure the intrafocal plate to the bone when intrafocal plate 10 is fully inserted and the insertion tool removed so as to allow plate element 10A of intrafocal plate 10 to snap against the bone. The use of screws 20 for either of the two intrafocal plates is optional and the decision of the physician performing the procedure.

Figure 6A:
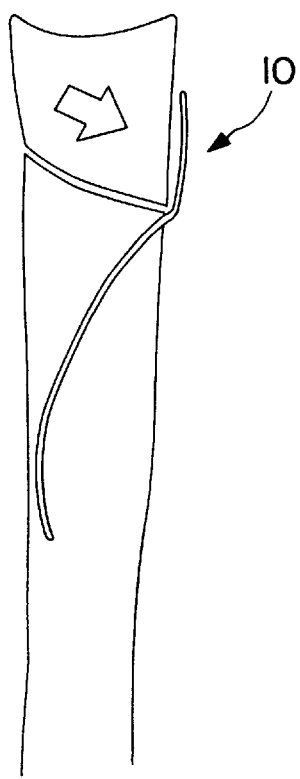
FIG. 6A of the drawings shows a schematic drawing of the intrafocal plate of FIGS. 1A, 1B inserted without a screw for a Colles fracture wherein the arrow shows the direction which the bone fragment would attempt to displace and which the intrafocal plate has been positioned to prevent.
Figure 6B:
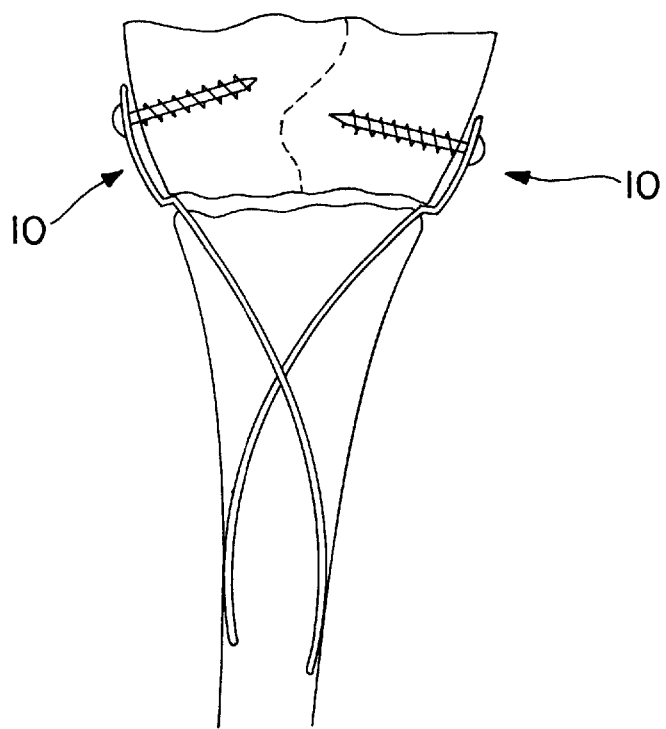
FIG. 6B of the drawings is a schematic view showing the use of two intrafocal plates of FIGS. 1A, 1B to address a transverse fracture of the proximal tibia which could tend to displace in either direction but which has been stabilized by the two intrafocal plates positioned on opposing sides of the bone.

FIG. 6A of the drawings shows intrafocal plate 10 inserted without a screw for a Colles fracture. The arrow depicted therein shows the direction which the upper bone fragment will try to displace and which intrafocal plate 10 is used in order to prevent. Intrafocal plate 10 can also be used in fractures where the direction of displacement is not preordained by the obliquity of the fracture as best shown in FIG. 6B. This transverse fracture of the proximal tibia may tend to displace in either direction, but can be stabilized with two intrafocal plates 10 as shown on opposing sides of the fractured bone. Further, if the dotted line shown in FIG. 6B represents yet another fracture splitting the end of the bone into two fragments, two intrafocal plates 10 from either side can be used to squeeze the two fragments together. Normally, another screw would be used to hold the two bone fragments together in addition to two intrafocal plates 10 and two screws 20, but intrafocal plates 10 may be used in order to get the reduction so that another screw can be inserted later.

Applicant believes that intrafocal plate 10 lends itself to use most commonly in the distal radius, like intrafocal pins are currently being used, but that intrafocal plates 10 can also be used in many other long bone locations in the body, such as the tibia and fibula, femur, ulna, humerus, metacarpal, metatarsal, and phalanges. Applicant further believes that most uses of intrafocal plate 10 would be for metaphyseal bone fractures (e.g., fractures near the end of the bone in the area of the junction between the tubular shaft and the spongy, blocky, ending of the bone known as the metaphysis or epiphysis). However, applicant does not intend to limit the use of the novel intrafocal plate to metaphyseal bone fractures since other uses may be found for the novel apparatus and method described herein before, and all such apparatuses and uses are intended to fall within the scope of the invention as set forth in the appended claims.

As previously observed, although screws 20 shown in FIG. 3 of the drawings may optionally be used with intrafocal plates 10 of the invention shown in FIGS. 1A, 1B and 2A, 2B, applicant does not believe that screws 20 are necessary to be used with intrafocal plates 10.

It will be understood that various details of the invention may be changed without departing from the scope of the invention. Furthermore, the foregoing description is for the purpose of illustration only, and not for the purpose of limitation—the invention being defined by the claims.

What is claimed is:

1. A longitudinally extending intrafocal plate for securing bone fractures, said intrafocal plate comprising a longitudinally extending plate element having a flat plate surface at one end thereof defining a top surface and a bottom-surface and a leading end and a trailing end, and having a longitudinally extending resilient body element connected at one end thereof to the trailing end of the flat plate surface so that said body element forms an acute angle with the flat plate surface and extends generally in the lengthwise direction of the flat plate surface and the other end of the body element defining a pin element, said intrafocal plate being formed so that a force applied at the pin element end causes a force to be applied in the opposite direction at the flat plate surface.

2. An intrafocal plate according to claim 1, wherein a shoulder is defined between the trailing end of the flat plate surface and the one end of the body element connected thereto.

3. An intrafocal plate according to claim 1, wherein the longitudinally extending resilient body element of said elongated plate element depends downwardly and outwardly from the bottom surface of the flat plate surface.

4. An intrafocal plate according to claim 1, wherein the flat plate surface defines one or more apertures therein.

5. An intrafocal plate according to claim 1, including one or more spike elements projecting from the bottom surface of the flat plate surface.

6. An intrafocal plate for securing bone fractures, said intrafocal plate comprising an elongated plate element having a flat plate surface at one end thereof defining a top surface and a bottom surface and a leading end and a trailing end, and having a longitudinally extending resilient body element connected at one end thereof to the trailing end of the flat plate surface and the other end of the body element defining a pin, said intrafocal plate being formed so that a force applied at the pin end causes a force to be applied in the opposite direction at the flat plate surface, said intrafocal plate including one or more screws for insertion through the one or more apertures in the flat plate surface in the flat plate surface.

7. A longitudinally extending intrafocal plate for securing metaphyseal bone fractures, said intrafocal plate comprising a longitudinally extending plate element having a flat plate surface at one end thereof with one or more apertures therein and defining a top surface and a bottom surface and a leading end and a trailing end, and having a longitudinally extending resilient body element depending from the trailing end of the flat plate surface so that the body element forms an acute angle with the flat plate surface and extends generally in the lengthwise direction of the flat plate surface, the body element defining a shoulder at one end at the juncture of the body element and the flat plate surface and an arcuate pin at the other end of the body element, said intrafocal plate being formed so that a force applied at the arcuate pin end causes a force to be applied in the opposite direction at the flat plate surface.

8. A longitudinally extending intrafocal plate for securing metaphyseal bone fractures, said intrafocal plate comprising a longitudinally extending plate element having a flat plate surface at one end thereof defining a top surface and a bottom surface and a leading end and a trailing end and including one or more spike elements projecting from the bottom surface of the flat plate surface, and having a longitudinally extending resilient body element depending from the trailing end of the flat plate surface so that the body element forms an acute angle with the flat plate surface and expends generally in the lengthwise direction of the flat plate surface, the body element defining a shoulder at one end at the juncture of the body element and the flat plate surface and an arcuate pin at the other end of the body element, said intrafocal plate being formed so that a force applied at the arcuate pin end causes a force to be applied in the opposite direction at the flat plate surface.

9. A method of treating metaphyseal bone fractures and the like with a percutaneous intrafocal plate system comprising the steps of:
   (a) providing an intrafocal plate comprising an elongated plate element having flat plate surface at one end thereof defining a leading end and a trailing end, and having a longitudinally extending resilient body element connected at one end thereof to the trailing end of the flat plate surface and the other end of the body element defining a pin;
   (b) inserting the pin end of said body element through a skin incision formed proximate to a metaphyseal bone fracture site and intrafocally inserting the pin end of said body element into the fracture site;
   (c) manipulating said elongated plate element as necessary to lever the fracture into a reduced position; and
   (d) pushing the body element portion of said elongated plate element into the tubular hollow of the fractured bone such that the pin end will resiliently contact the inside wall surface defining the tubular hollow at a site opposing the fracture site and cause said intrafocal plate to seat in the fracture site and urge the flat plate surface of said elongated plate element against the outside surface of the bone.

10. A method according to claim 9, wherein the pin end is inserted into the fracture site at a 180 degree relative rotation to the position at which it will finally lie and then rotated 180 degrees to better manipulate said elongated plate element to lever the fracture into a reduced position.

11. A method according to claim 9, including securing said elongated plate element of said intrafocal plate to the bone with one or more screws.

12. A method of treating metaphyseal bone fractures and the like with a percutaneous intrafocal plate system comprising the steps of:
   (a) providing an intrafocal plate comprising an elongated plate element having flat plate surface at one end thereof defining a leading end and a trailing end, and having a longitudinally extending resilient body element depending from the trailing end of the flat plate surface defining a shoulder at one end at the juncture of the body element and the flat plate surface and a pin at the other end of the body element;
   (b) inserting the pin end of said body element through a skin incision formed proximate to a metaphyseal bone fracture site and intrafocally inserting the pin end of said body element into the fracture site at a 180 degree rotation relative to the position at which it will finally lie;
   (c) rotating said elongated plate element 180 degrees and manipulating said elongated plate element as necessary to lever the fracture into a reduced position; and
   (d) pushing the body element position of said elongated plate element into the tubular hollow of the fractured bone such that the pin will resiliently contact the inside wall surface defining the tubular hollow at a site opposing the fracture site and cause the shoulder of said elongated plate element to seat in the fracture site and urge the flat plate surface of said elongated plate element against the outside surface of the bone.

13. A method according to claim 12, including securing said elongated plate element of said intrafocal plate to the bone with one or more screws.

14. A method of treating metaphyseal bone fractures and the like with a percutaneous intrafocal plate system comprising the steps of:
   (a) providing an intrafocal plate comprising an elongated plate element having flat plate surface at one end thereof defining a leading end and a trailing end, and having a longitudinally extending resilient body element depending from the trailing end of the flat plate surface defining a shoulder at one end at the juncture of the body element and the flat plate surface and a pin at the other end of the body element, said bottom surface of said flat plate surface including one or more spike elements projecting therefrom;
   (b) inserting the pin end of said body element through a skin incision formed proximate to a metaphyseal bone fracture site and intrafocally inserting the pin end of said body element into the fracture site;
   (c) manipulating said elongated plate element as necessary to lever the fracture into a reduced position; and
   (d) pushing the body element position of said elongated plate element into the tubular hollow of the fractured bone such that the pin will resiliently contact the inside wall surface defining the tubular hollow at a site opposing the fracture site and cause the shoulder of said elongated plate element to seat in the fracture site and urge the flat plate surface of said elongated plate element against the outside surface of the bone.

15. A method according to claim 14, wherein the pin end is inserted into the fracture site at a 180 degree relative rotation to the position at which it will finally lie and then rotated 180 degrees to better manipulate said elongated plate element to lever the fracture into a reduced position.

\* \* \* \* \*